US00PP22174P2

(12) United States Plant Patent
Boe

(10) Patent No.: US PP22,174 P2
(45) Date of Patent: Oct. 4, 2011

(54) ***THUJA* PLANT NAMED 'ART BOE'**

(50) Latin Name: *Thuja occidentalis*
Varietal Denomination: Art Boe

(75) Inventor: Arthur Boe, Faribault, MN (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/807,631

(22) Filed: Sep. 9, 2010

(51) Int. Cl.
*A01H 5/00* (2006.01)

(52) U.S. Cl. ..... Plt./213

(58) Field of Classification Search ..... Plt./213
See application file for complete search history.

*Primary Examiner* — Kent L Bell
(74) *Attorney, Agent, or Firm* — C. A. Whealy

(57) ABSTRACT

A new and distinct cultivar of *Thuja* plant named 'Art Boe', characterized by its upright and narrowly conical plant habit; vigorous growth habit; freely branching habit; green-colored leaves that do not winter burn; and good winter hardiness.

2 Drawing Sheets

Botanical designation: *Thuja occidentalis.*
Cultivar denomination: 'ART BOE'.

BACKGROUND OF THE INVENTION

The present invention relates to a new and distinct cultivar of *Thuja* plant, botanically known as *Thuja occidentalis*, and hereinafter referred to by the name 'Art Boe'.

The new *Thuja* plant is a product of a planned breeding program conducted by the Inventor in Faribault, Mich. The objective of the breeding program is to create new narrowly conical *Thuja* plants with good winter hardiness.

The new *Thuja* plant originated from an open-pollination in 1998 in Faribault, Mich. of *Thuja occidentalis* 'Hetz Wintergreen', not patented, as the female, or seed, parent with an unknown selection of *Thuja occidentalis*, as the male, or pollen, parent. The new *Thuja* plant was discovered and selected by the Inventor as a single plant within the progeny of the stated open-pollination in a controlled environment in Faribault, Mich. in 2001.

Asexual reproduction of the new *Thuja* plant by hardwood cuttings in a controlled environment in Faribault, Mich. since 2001, has shown that the unique features of this new *Thuja* plant are stable and reproduced true to type in successive generations.

SUMMARY OF THE INVENTION

Plants of the new *Thuja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Art Boe'. These characteristics in combination distinguish 'Art Boe' as a new and distinct cultivar of *Thuja* plant:

1. Upright and narrowly conical plant habit.
2. Vigorous growth habit.
3. Freely branching habit.
4. Green-colored leaves that do not winter burn.
5. Good winter hardiness.

Plants of the new *Thuja* can be compared to plants of the female parent, 'Hetz Wintergreen'. Plants of the new *Thuja* differ primarily from plants of 'Hetz Wintergreen' in plant habit as plants of the new *Thuja* are narrower than plants of 'Hetz Wintergreen'.

Plants of the new *Thuja* can be compared to plants of *Thuja occidentalis* 'Emerald', not patented. Plants of the new *Thuja* differ from plants of 'Emerald' in the following characteristics:

1. Plants of the new *Thuja* are narrower than plants of 'Emerald'.
2. Plants of the new *Thuja* have darker green-colored foliage than plants of 'Emerald'.
3. Leaves of plants of the new *Thuja* do not winter burn whereas leaves of plants of 'Emerald' winter burn.
4. Plants of the new *Thuja* were more winter hardy than plants of 'Emerald'.

BRIEF DESCRIPTION OF THE PHOTOGRAPHS

The accompanying colored photographs illustrate the overall appearance of the new *Thuja* plant showing the colors as true as it is reasonably possible to obtain in colored reproductions of this type. Colors in the photograph may differ slightly from the color values cited in the detailed botanical description which accurately describe the colors of the new *Thuja* plant.

The photograph on the first sheet comprises a side perspective view of a typical plant of 'Art Boe' grown in an outdoor nursery.

The photograph on the second sheet is a close-up view of a typical plant of 'Art Boe'.

DETAILED BOTANICAL DESCRIPTION

The aforementioned photographs and following observations, measurements and values describe plants grown in outdoor nurseries in Faribault and Grand Haven, Mich. and under conditions which closely approximate commercial *Thuja* plant production. Plants were three years old when the photographs and description were taken. In the following detailed description, color references are made to The Royal Horticultural Society Colour Chart, 2001 Edition, except where general terms of ordinary dictionary significance are used.

Botanical classification: *Thuja occidentalis* 'Art Boe'.

Parentage:

*Female, or seed, parent.*—*Thuja occidentalis* 'Hetz Wintergreen', not patented.

*Male, or pollen, parent.*—Unknown selection of *Thuja occidentalis*, not patented.

Propagation:

*Type.*—By hardwood cuttings.

*Time to initiate roots, winter.*—About three months at 10° C.

*Time to produce a rooted young plant, winter.*—About ten months at 10° C.

*Root description.*—Thick and fine; brown and cream in color.

*Rooting habit.*—Freely branching; dense.

Plant description:

*Plant and growth habit.*—Perennial coniferous shrub; upright and narrowly conical plant habit; vigorous growth habit.

*Plant height.*—About 1.5 meters.

*Plant diameter.*—About 35 cm.

*Branching habit.*—Freely branching with numerous lateral branches; dense and bushy habit.

*Lateral branch description.*—Length: About 16 cm. Diameter: About 4 mm. Internode length: Less than 1 mm. Strength: Strong. Texture: Smooth. Color: Developing branches: Close to 144B. Developed branches: Close to 177A.

*Leaf description.*—Appearance/arrangement: Flattened and appressed, scale-like; opposite, simple; sessile. Length: About 1 mm. Width: About 1 mm. Shape: Ovate to oblanceolate. Apex: Abruptly pointed. Base: Obtuse. Margin: Entire. Venation pattern: Veins are not visible. Fragrance: Cedar-like. Texture: Smooth, glabrous. Color: Developing leaves, upper and lower surfaces: Close to 143A. Fully expanded leaves, upper and lower surfaces: Close to 141A; leaves do not winter burn.

Cone description: Cone development has not been observed on plants of the new *Thuja*.

Temperature tolerance: Plants of the new *Thuja* have been observed have good winter hardiness and to tolerate temperatures from about −35° C. to about 36° C.

Pathogen/pest resistance: Plants of the new *Thuja* have not been observed to be resistant to pests and pathogens common to *Thuja* plants.

It is claimed:

1. A new and distinct *Thuja* plant named 'Art Boe' as illustrated and described.

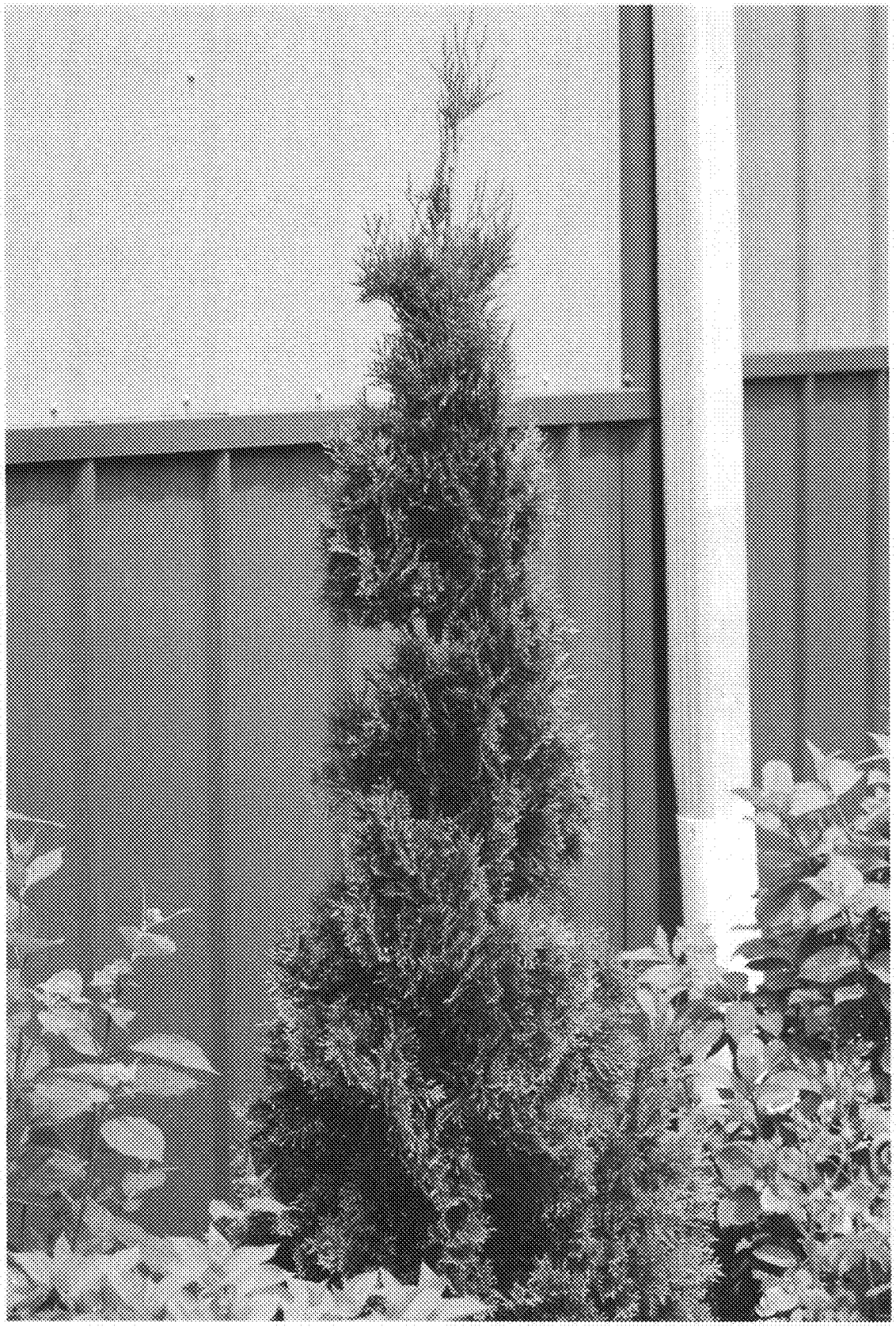

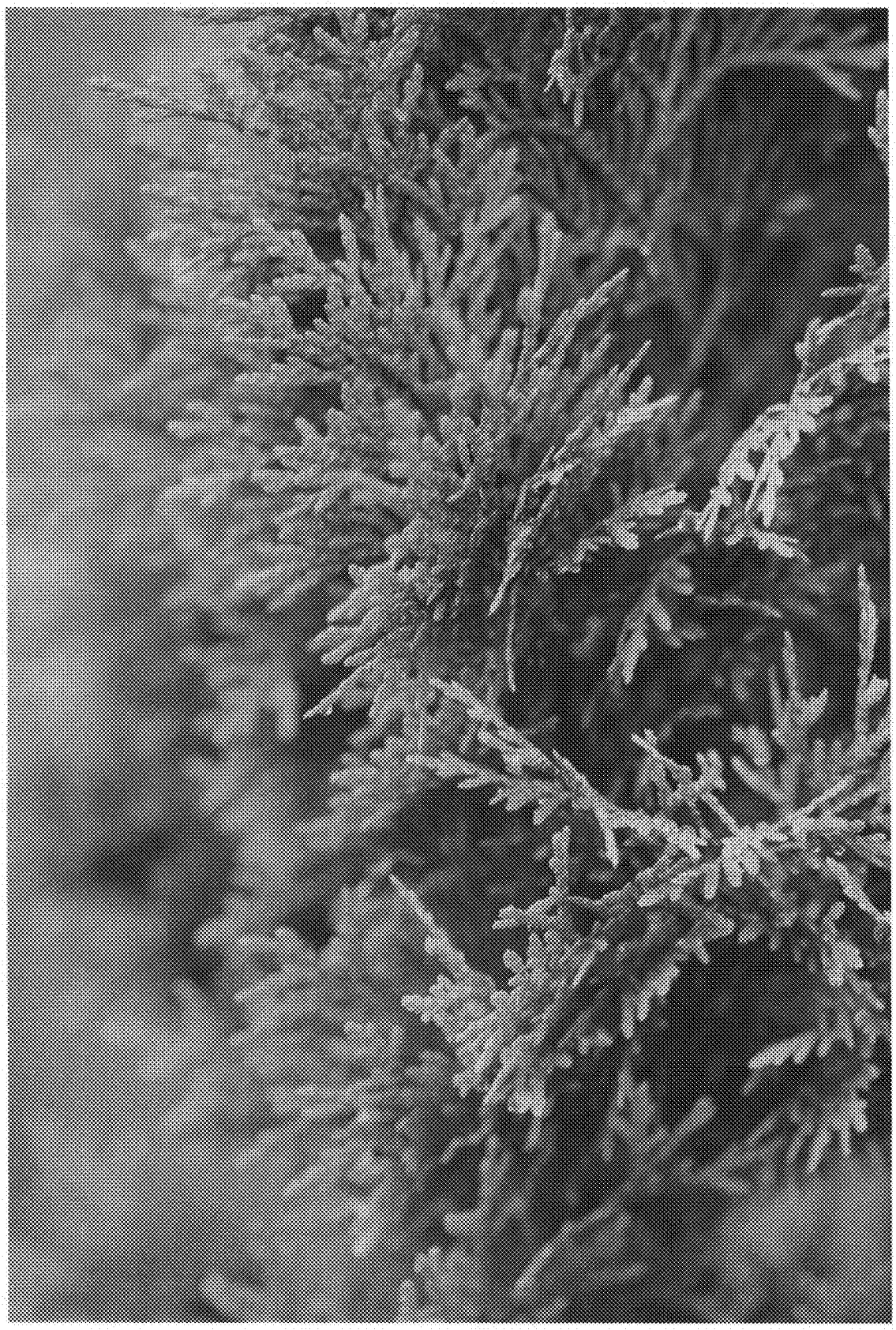

* * * * *